US00PP16268P2

(12) United States Plant Patent
Kordes

(10) Patent No.: US PP16,268 P2
(45) Date of Patent: Feb. 21, 2006

(54) MINIATURE ROSE PLANT NAMED 'KORNILSCA'

(50) Latin Name: *Rosa hybrida*
Varietal Denomination: KORnilsca

(75) Inventor: Tim-Hermann Kordes, Offenseth-Sparrieshoop (DE)

(73) Assignee: W. Kordes' Söhne Rosenschnlen GmbH & Co KG, Klein Offenseth-Sparrieshoop (DE)

( * ) Notice: Subject to any disclaimer, the term of this patent is extended or adjusted under 35 U.S.C. 154(b) by 60 days.

(21) Appl. No.: 10/737,663

(22) Filed: Dec. 15, 2003

(51) Int. Cl.
*A01H 5/00* (2006.01)

(52) U.S. Cl. ..... Plt./121
(58) Field of Classification Search ..... Plt./121, Plt./116, 120, 128
See application file for complete search history.

(56) References Cited

FOREIGN PATENT DOCUMENTS

QZ 20022093 * 12/2002

QZ 12902 * 4/2004

OTHER PUBLICATIONS

Application for PBR in EU (GS–90 235) Dec. 16, 2002, 9 pages.*

Application for PBR in EU (GS–90 235) Dec. 16, 2002, 9 pages.

QZ 2002/2093 (CPVO PBR completed application acceptance form) Dec. 20, 2002, 2 pages.

QZ 12902 (CPVO PBR Grant) Apr. 5, 2004, 2 pages.

* cited by examiner

*Primary Examiner*—Anne Marie Grunberg
*Assistant Examiner*—June Hwu

(57) ABSTRACT

A new and distinct variety of miniature rose with abundant, pink flowers and dark green and attractive foliage. The new variety propagates well from cuttings and by grafting. It exhibits uniform growth and flowering under less than ideal environmental conditions in greenhouse, nursery, and garden culture. This new and distinct variety has shown to be uniform and stable in the resulting generations from asexual propagation.

1 Drawing Sheet

Genus, species and variety denomination: The botanical classification of the new rose plant is *Rosa hybrida*, variety denomination 'KORnilsca'.

BACKGROUND OF THE INVENTION

The new variety of miniature rose plant of the present invention originated from a controlled crossing in a breeding program between 'KORkleiva', a patented rose described and illustrated in U.S. Plant Pat. No. 11,232 issued on Feb. 22, 2000 and 'Scarletta Kordana' a non patented rose variety. The two parents were crossed and the resulting seeds were planted in a controlled greenhouse environment.

As part of their rose development program, Tim-Hermann Kordes germinated the seeds from the aforementioned hybridization and conducted evaluations and observations on the resulting seedlings in a controlled environment in Sparrieshoop, Germany. The resulting seedlings exhibited distinctive physical and biological characteristics. The new rose plant was selected in June, 2000 as a single plant from the seedling beds due to its superior characteristics and asexually propagated for further evaluation. This new and distinctive miniature rose variety is named 'KORnilsca'.

SUMMARY OF THE INVENTION

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers.

This combination of traits is not present in prior rose cultivars. These objectives have been substantially achieved and distinguish 'KORnilsca' from all other varieties of which we are aware.

The new rose plant may be distinguished from its seed parent, KORkleiva, by the following combination of characteristics:

1. The seed parent exhibits cream colored flowers, while KORnilsca has pink flowers.
2. The seed parent has approximately 25–30 petals while KORnilsca has 50–55 petals.

The new rose plant may be distinguished from its pollen parent, Scarletta Kordana by the following combination of characteristics:

1. The pollen parent exhibits red colored flowers with 15–20 petals, while KORnilsca has pink flowers with over 50 petals.

2. The pollen parent exhibits smaller flowers than KORnilsca.

Asexual reproduction of 'KORnilsca' by softwood cuttings in greenhouse was first done Jul. 1, 2000 in Odense, Denmark. This initial and subsequent propagations conducted in controlled environments show that the foregoing and all other characteristics of 'KORnilsca' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORnilsca'. Specifically illustrated in sheet one.

DETAILED DESCRIPTION

Figures 1, 2, 3, 4, 5, 6, 7, 8, 9, 10:
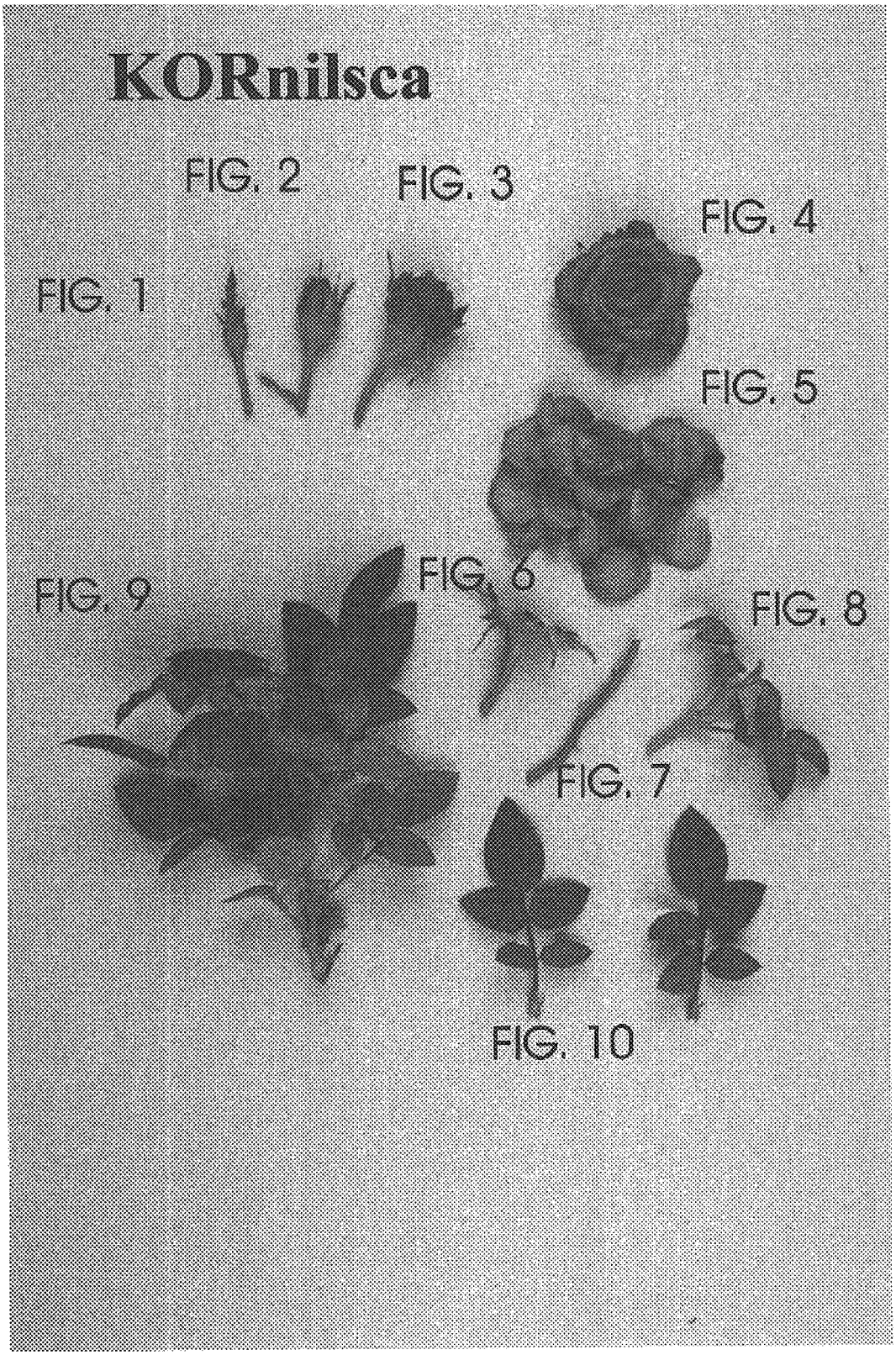
FIG. 1. Tight flower bud.
FIG. 2. Partially opened bud.
FIG. 3. Half open bloom.
FIG. 4. Open bloom.
FIG. 5. Flower petals, detached.
FIG. 6. Sepals, receptacle, and pedicel.
FIG. 7. Stem exhibiting thorns.
FIG. 8. New growth.
FIG. 9. Stem showing branching and the attachment of leaves.
FIG. 10. Single leaves.

The following is a description of 'KORnilsca', as observed in its growth in glasshouses in Odense Denmark on plants of 12 weeks of age and in a field nursery in Sparrieshoop, Germany on plants of 1 year of age. Color references are made using The Royal Horticultural Society (London, England) Colour Chart, 2001 except where common terms of color are used.

For a comparison, several physical characteristics of the rose variety 'KORfrauma', a rose variety from the same inventor described and illustrated in U.S. Plant Pat. No. 11,363 and issued on Apr. 25, 2000 are compared to 'KORnilsca' in Chart 1.

CHART 1

| | 'KORnilsca' | 'KORfrauma' |
|---|---|---|
| Bud color, as sepals divide. | Red Group 54A–48A. | Red Group 53B. |
| Average size of receptacle. | Large. 7–8 mm (h) 10–11 mm (w). | Small. 5.5 mm (h) 6.35 mm (w). |
| Average open bloom diameter. | 50 mm. | 38 mm. |

Parents:

*Seed parent.*—KORkleiva.

*Pollen parent.*—Scarletta Kordana.

Classification:

*Botanical classification.*—*Rosa hybrida.*

*Commercial classification.*—Miniature.

FLOWER AND FLOWER BUD

Blooming habit: Recurrent.

Flower bud:

*Size.*—Upon opening, 22–25 mm in length from base of receptacle to end of bud.

*Bud form.*—Pointed ovoid to globular.

*Bud color.*—As sepals first unfold, bud color is Red Group 54A. When ¼ open, the upper surface of petals is Red Group 54A–B., and the lower surface is Red Group 54A–B.

*Sepals.*—Size: Average 18–20 mm long×4–6 mm wide. Margins: Weak foliaceous appendages on three of the five sepals. Quantity: Five. Surface texture: Pubescent. Stipitate glands are generally lacking. Color: Upper surface Green Group 138A. Lower surface Green Group 138A.

Receptacle:

*Surface.*—Covered with short, fine white hairs.

*Color.*—Yellow-Green Group 146B.

*Shape.*—Broadly funnel shaped.

*Size.*—7–8 mm (h) 10–11 mm (w).

Peduncle:

*Surface.*—Smooth, with limited numbers of fine, white hairs and moderate numbers of stipitate glands.

*Length.*—25–30 mm average length.

*Diameter.*—1.6–1.8 mm.

*Color.*—Yellow-Green Group 146B.

*Strength.*—Upright and strong.

Borne: Most often singly, however some with up to 4 buds.

Flower bloom:

*Fragrance.*—Light.

*Duration.*—The blooms have a duration on the plant of approximately 21 to 24 days. As a cut flower 10 to 14 days.

*Size.*—Large for a 8–11 cm pot rose. Average flower diameter is 50 mm when open.

*Form.*—Shape of flower when viewed from the side: Upon opening, upper part: Convex. Upon opening, lower part: Flattened convex to convex. Open flower, upper part: Flattened convex. Open flower, lower part: Flattened convex.

Color:

*Upon opening, petals.*—Outermost petals: Outer Side: Red Group 54B. Inner Side: Red Group 55A–B. Innermost petals: Outer Side: Red Group 54A–B. Inner Side: Red Group 55A.

*Upon opening, basal petal spots.*—Outer Side: White Group 155A. Inner Side: White Group 155A. Basal petal spot, innermost petals: Outer Side: White Group 155A. Inner Side: White Group 155A.

*After opening, petals.*—Outermost petals: Outer Side: Red Group 54B. Inner Side: Red Group 55A–B. Innermost petals: Outer Side: Red Group 54A–55A. Inner Side: Red Group 54A–55A.

*After opening, basal petal spots.*—Basal petal spot, outermost petals: Outer Side: White Group 155A. Inner Side: White Group 155A. Basal petal spot, innermost petals: Outer Side: White Group 155A. Inner Side: White Group 155A.

*Variegations.*—Occasional greenish streak of Green-White Group 157A on the guard petals.

General tonality: On open flower Red Group 51B. No change in the general tonality at the end of the $6^{th}$ day. Afterwards, general tonality is Red Group 51C.

Petals:

*Petal count.*—Approximately 50 to 55 petals under normal conditions.

*Petal reflex.*—Petals reflex somewhat.

*Petal edge.*—Entire.

*Petal shape.*—Round. Shape of Base: Round. Shape of Apex: Round.

*Petal size.*—12–20 mm long; 8–20 mm wide. Petal width decreases closer to center of bloom.

*Thickness.*—Average to above average.

*Surface texture.*—Nearly smooth.

*Petal arrangement.*—Generally in a regular pattern with overlapping edges.

*Petaloids.*—Present. Average of 5–10 per flower. Petaloids are 5–6 mm long and 2–3 mm wide. Color of inner side is Red Group 54A. Color of outer side is Red Group 55A.

Reproductive organs:

*Pistils.*—Present. Usually not upright due to the presence of so many petals and petaloids. Stigmas: Location: Superior in location to anthers. Color: Green-White Group 157A. Styles: Length: 3–5 mm long. Color: Green-White Group 157A. Limited intonation immediately below the stigma of Greyed-Purple Group 185C.

*Stamens.*—Approximately 50–60 on average and regularly arranged around the styles. Anthers: Size: 1–2 mm long. Color: Yellow-Orange Group 21B–C. Quantity: Approximately 50–60. Pollen: Average quantity present. Color: Yellow-Orange Group 21B–C. Filaments: Color: Yellow-Green Group 154D. Length: 2–3 mm.

THE PLANT

Plant growth: Vigorous. Upright to bushy. When grown as a 8–11 cm pot plant, the average height of the plant itself is 18–20 cm and the average width is 18–20 cm. When grown as a budded nursery plant the average plant height is 30 cm and the average plant width is 20–25 cm.

Stems:

*Stem color.*—Young wood: Green Group 138A. Older wood: Green Group 138A.

*Stem surface.*—Young wood: Smooth. Older wood: Smooth.

Prickles: Present.

*Incidence.*—Average of 2–5 per 10 cm of stem.

*Size.*—Average length: 2 mm–5 mm.

*Color.*—Green-Yellow Group 161D with intonations of Greyed-Orange Group 168D.

*Shape.*—Linear.

Leaves and leaflets: Normally 5 leaflets on normal leaves in middle of the stem. Some leaves with 7 leaflets.

*Leaf size.*—75 mm (l)×50 mm (w).

*Quantity.*—Abundant.

*Glossiness on upper side.*—Weak.

*Color, mature foliage.*—Upper Leaf Surface: Green Group 138A–139A. Lower Leaf Surface: Green Group 138B.

*Color, juvenile foliage.*—Upper Leaf Surface: Green Group 138A–139A. Lower Leaf Surface: Green Group 138B.

*Anthocyanin intonation.*—Present. Intonations present on leaf margins of developing leaves.

Stipules: Size: 10 mm–12 mm.

*Stipule color.*—Green Group 138A.

*Presence of stipitate glands.*—Present on margins.

Petiole: With a limited number of white hairs and stipitate glands underneath.

*Length.*—12 mm.–16 mm.

*Diameter.*—1.6–1.8 mm.

*Petiole color.*—Green Group 138A–139A. Intonations of Greyed-Red Group 181A on margins.

*Prickles.*—1–2 small prickles present underneath. Green-White Group 157A. Length 1–1.5 mm.

*Stipitate glands.*—Present on margins.

Rachis:

*Rachis color.*—Green Group 138A. Intonations of Greyed-Red Group 181A on margins.

*Prickles.*—1–2 small prickles present underneath. Green-White Group 157A. Length 1–1.5 mm.

Leaflets:

*Average leaflet.*—Pointed oval.

*Average size of terminal leaflet.*—32–36 mm long; 20–24 mm wide.

*Margins.*—Serrated.

*Texture.*—Thin to medium.

Hips/seed formation: None observed. The plant has not been grown to the stage of hip and seed development due to its use as a flowering potted plant.

Winter hardiness: Due to the variety's principal use in greenhouses, winter hardiness has not been evaluated.

Disease resistance: Above average resistance to mildew and *Botrytis* under normal growing conditions in Odense, Denmark.

I claim:

1. A new and distinct variety of miniature rose plant characterized by the following combination of characteristics:

(a) forms abundant, attractive pink long lasting flowers;

(b) exhibits a compact and bushy growth habit;

(c) is suited for growing in greenhouse in pots from softwood cutting, and;

(d) exhibits durable flowers and foliage suitable for distribution in the floral industry;

substantially as herein illustrated and described.

* * * * *

KORnilsca